(12) United States Patent
Itonaga et al.

(10) Patent No.: US 11,867,697 B2
(45) Date of Patent: Jan. 9, 2024

(54) PANCREATIC CANCER DETECTION METHOD AND PANCREATIC CANCER DETECTION KIT

(71) Applicants: JVCKENWOOD Corporation, Yokohama (JP); KEIO UNIVERSITY, Tokyo (JP)

(72) Inventors: Makoto Itonaga, Yokohama (JP); Masayuki Ono, Yokosuka (JP); Takahiro Yokose, Tokyo (JP); Atsushi Matsuda, Tokyo (JP); Yasuaki Kabe, Tokyo (JP); Sachiko Matsuda, Tokyo (JP); Miwa Hirai, Tokyo (JP); Minoru Kitago, Tokyo (JP)

(73) Assignees: JVCKENWOOD CORPORATION, Yokohama (JP); KEIO UNIVERSITY, Tokyo (JP)

( * ) Notice: Subject to any disclaimer, the term of this patent is extended or adjusted under 35 U.S.C. 154(b) by 87 days.

(21) Appl. No.: 17/404,717

(22) Filed: Aug. 17, 2021

(65) Prior Publication Data
US 2022/0065858 A1     Mar. 3, 2022

(30) Foreign Application Priority Data

Sep. 1, 2020  (JP) ................................ 2020-147108

(51) Int. Cl.
G01N 33/574    (2006.01)
(52) U.S. Cl.
CPC ... G01N 33/5748 (2013.01); G01N 33/57438 (2013.01)

(58) Field of Classification Search
CPC .................... G01N 33/5748; G01N 33/57438
See application file for complete search history.

(56) References Cited

PUBLICATIONS

Scientifically Based Pancreatic Cancer Diagnostic Guidelines 2009 Edition, Editing Japan Pancreas Society Pancreatic Cancer Diagnosis Guideline Revision Committee, CQ1-3 "What is the first examination to do if pancreatic cancer is suspected?", retrieved on Jul. 10, 2020. Partial translation.
Takahiro Yokose et al., O-Glycan-Altered Extracellular Vesicles: A Specific Serum Marker Elevated in Pancreatic Cancer, Cancers 2020, 12, 2469, including Supplementary Materials.

*Primary Examiner* — Peter J Reddig
*Assistant Examiner* — Cheng Lu
(74) *Attorney, Agent, or Firm* — Procopio, Cory, Hargreaves & Savitch LLP

(57) ABSTRACT

A pancreatic cancer detection method is provided, including: (a) bringing extracellular vesicles, which are in a body fluid sample derived from a subject into contact with one or more kinds of lectins; (b) measuring an amount of the extracellular vesicles bound to the one or more kinds of lectins after (a); and (c) evaluating the presence of pancreatic cancer in the subject based on the amount of the extracellular vesicles measured in (b). In addition, a pancreatic cancer detection kit is provided, including: a solid-phase carrier on which one or more kinds of lectins are immobilized; and an antibody specifically binding to a pan-extracellular vesicle membrane protein or an antigen-binding fragment thereof.

10 Claims, 7 Drawing Sheets

PANCREATIC CANCER DETECTION METHOD AND PANCREATIC CANCER DETECTION KIT

BACKGROUND OF THE INVENTION

Field of the Invention

The present invention relates to a pancreatic cancer detection method and a pancreatic cancer detection kit.

Priority is claimed on Japanese Patent Application No. 2020-147108, filed Sep. 1, 2020, the content of which is incorporated herein by reference.

Description of Related Art

The number of deaths from pancreatic cancer is increasing year by year. According to the statistics on the death toll from cancer in Japan in 2018, pancreatic cancer was the fourth leading cause of death with 33,475 deaths. In recent years, not only improvements in surgical procedures themselves, but also multidisciplinary treatment strategies such as preoperative treatment (such as chemotherapy or radiotherapy) and postoperative adjuvant therapy have been developed. For this reason, although an improvement in long-term results has been recognized compared to before, there are still many problems with malignant neoplasms as a whole. The reasons for this are that, for example, pancreatic cancer is often diagnosed as advanced cancer despite the development of image diagnosis, has a high rate of recurrence even if radical resection is achieved through a high-difficulty surgical operation since the resection rate at diagnosis is about 30%, and has resistance to therapy through an existing chemotherapy or radiation therapy.

One of the reasons early diagnosis of pancreatic cancer is difficult is the peculiarity of the organ from which it is difficult to directly collect a sample compared to organs with other carcinomas. Although the diagnostic accuracy has improved due to the improvement in the resolution of image inspection, no effective screening method for pancreatic cancer has been established. In addition, although diagnostic ability has improved due to widespread use of an endoscopic ultrasound fine needle aspiration (EUS-FNA) method when collecting tissue, there are problems of invasiveness and the possibility of seeding through puncture, and a simpler, less-invasive pancreatic cancer inspection method is required.

An inspection method such as a liquid biopsy for performing diagnosis of cancer or determination of a therapeutic effect by examining cancer-derived molecules using a body fluid (such as blood) sample is attracting attention in pancreatic cancer.

Examples of existing tumor markers for detecting pancreatic cancer which have been used for liquid biopsies include CA19-9, Span-1, CA50, CA242, Dupan-2, TAG-72, and urinary fucose as glycan antigens and CEA, POA, and TPS as antigens other than those of sugar chains (Non-Patent Literature 1). Although these tumor markers have favorable sensitivity, there is a problem in that they do not have higher specificity and have a high pseudopositive rate. Furthermore, the positive predictive value of pancreatic cancer is generally low except for advanced cancer, and the positive predictive value of CA19-9 even for pancreatic cancer of 2 cm or less is merely 52%, which is approximately half. For this reason, tumor markers have a problem in detecting early-stage pancreatic cancer.

PATENT DOCUMENTS

[Non-Patent Document 1] Committee for Revision of Clinical Guidelines for Pancreatic Cancer of Japan Pancreas Society, Diagnosis "CQ1 Diagnosis, CQ1-3 What Is the First Step When Pancreatic Cancer Is Suspected?" of Clinical Guidelines for Pancreatic Cancer 2009, [Online], [Search on Jul. 10, 2020], the Internet <URL: http://www.suizou.org/PCMG2009/cq1/cq1-3.html>

SUMMARY OF THE INVENTION

A simple, less-invasive inspection method is required for early diagnosis of pancreatic cancer. However, in liquid biopsies in which tumor markers in the related art are used, the positive predictive value of pancreatic cancer is generally low and it is difficult to detect early-stage pancreatic cancer.

Therefore, an object of the present invention is to provide a pancreatic cancer detection method and a pancreatic cancer detection kit which enable early detection of pancreatic cancer and monitoring of a therapeutic effect through a liquid biopsy.

The present invention has the following aspects.

[1] A pancreatic cancer detection method, including: (a) bringing extracellular vesicles, which are in a body fluid sample derived from a subject, into contact with one or more kinds of lectins; (b) measuring an amount of the extracellular vesicles bound to the one or more kinds of lectins after (a); and (c) evaluating presence of pancreatic cancer in the subject based on the amount of the extracellular vesicles measured in (b).

[2] The pancreatic cancer detection method according to [1], in which (c) includes evaluating that pancreatic cancer is present in the subject in a case where the amount of the extracellular vesicles measured in (b) is larger than that of extracellular vesicles binding to the one or more kinds of lectins measured using a body fluid sample from a subject known to not have pancreatic cancer.

[3] The pancreatic cancer detection method according to [1] or [2], in which the one or more kinds of lectins include at least one selected from the group consisting of DSA (*Datura stramonium* agglutinin), STL (*Solanum tuberosum* lectin), LEL (*Lycopersicon esculentum* lectin), ACA (*Amaranthus caudatus* agglutinin), UDA (*Urtica dioica* agglutinin), ABA (*Agaricus bisporus* agglutinin), MAH (*Maackia amurensis* hemagglutinin), and TJA-1 (*Trichosanthes japonica* agglutinin I).

[4] The pancreatic cancer detection method according to any one of [1] to [3], in which Step (b) is performed using an antibody specifically binding to a pan-extracellular vesicle membrane protein or an antigen-binding fragment thereof.

[5] The pancreatic cancer detection method according to [4], in which the pan-extracellular vesicle membrane protein is selected from the group consisting of CD9, CD63, and CD81.

[6] A pancreatic cancer detection kit, including: a solid-phase carrier on which one or more kinds of lectins are immobilized; and an antibody specifically binding to a pan-extracellular vesicle membrane protein or an antigen-binding fragment thereof.

[7] The pancreatic cancer detection kit according to [6], in which the one or more kinds of lectins include at least one selected from the group consisting of DSA, STL, LEL, ACA, UDA, ABA, MAH, and TJA-1.

[8] The pancreatic cancer detection kit according to [6] or [7], in which the pan-extracellular vesicle membrane protein is selected from the group consisting of CD9, CD63, and CD81.

[9] The pancreatic cancer detection kit according to any one of [6] to [8], in which the antibody specifically binding to a pan-extracellular vesicle membrane protein or the antigen-binding fragment thereof is immobilized on a solid-phase carrier particle.

[10] The pancreatic cancer detection kit according to any one of [6] to [9], further including: an extracellular vesicle capture unit used in an extracellular vesicle counter used for counting extracellular vesicles, in which the solid-phase carrier is provided in the extracellular vesicle capture unit.

[11] A method for treating pancreatic cancer: (a) bringing extracellular vesicles, which are in a body fluid sample derived from a subject, into contact with one or more kinds of lectins; (b) measuring an amount of the extracellular vesicles bound to the one or more kinds of lectins after (a); (c) identifying the subject having pancreatic cancer based on the amount of the extracellular vesicles measured in (b); and (d) treating the pancreatic cancer in the subject having pancreatic cancer who is identified in (c).

[12] The method according to [11], wherein (c) comprises identifying the subject in which the amount of the extracellular vesicles measured in (b) is larger than that of extracellular vesicles binding to the one or more kinds of lectins measured using a body fluid sample from a subject known to not have pancreatic cancer, as the subject having pancreatic cancer.

[13] The method according to [11] or [12], wherein the one or more kinds of lectins include at least one selected from the group consisting of DSA, STL, LEL, ACA, UDA, ABA, MAH, and TJA-1.

[14] The method according to any one of [11] to [13], wherein (b) is performed using an antibody specifically binding to a pan-extracellular vesicle membrane protein or an antigen-binding fragment thereof.

[15] The method according to [14], wherein the pan-extracellular vesicle membrane protein is selected from the group consisting of CD9, CD63, and CD81.

According to the present invention, a pancreatic cancer detection method and a pancreatic cancer detection kit are provided which enable early detection of pancreatic cancer and monitoring of a therapeutic effect through a liquid biopsy.

DETAILED DESCRIPTION OF THE INVENTION

Figure 1A:
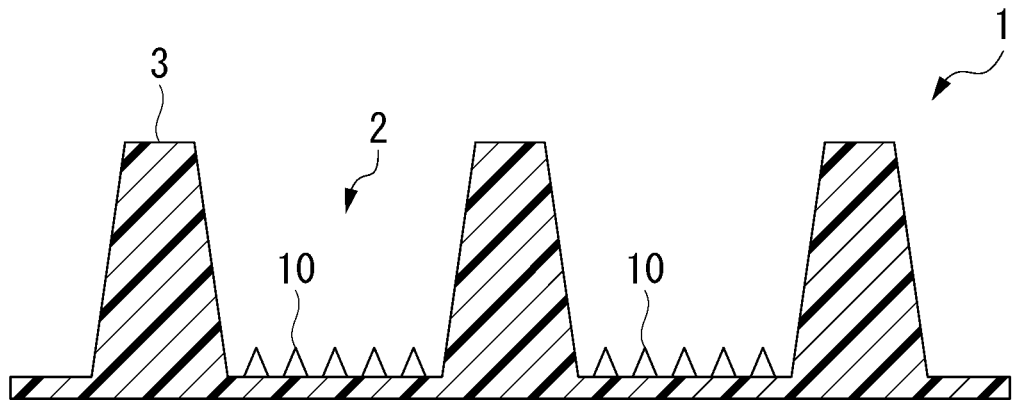
FIG. 1A shows an example of a solid-phase carrier on which lectins used in a pancreatic cancer detection method according to one embodiment of the present invention are immobilized.

Hereinafter, an embodiment of the present invention will be described in detail with reference to the drawings according to circumstances. In the drawings, the same or corresponding portions will be denoted by the same or corresponding reference numerals, and description thereof will not be repeated. The dimensional ratio in each drawing is exaggerated for explanation and does not necessarily coincide with the actual dimensional ratio.

(Pancreatic Cancer Detection Method)

In one embodiment, the present invention provides a pancreatic cancer detection method. A pancreatic cancer detection method of the present embodiment includes: Step (a) of bringing extracellular vesicles, which are in a body fluid sample derived from a subject, into contact with one or more kinds of lectins; Step (b) of measuring an amount of the extracellular vesicles bound to the one or more kinds of lectins after Step (a); and Step (c) of evaluating presence of pancreatic cancer in the subject based on the amount of the extracellular vesicles measured in Step (b).

The outline of the pancreatic cancer detection method of the present embodiment will be described with reference to FIGS. 1A to 1C.

Figure 1B:
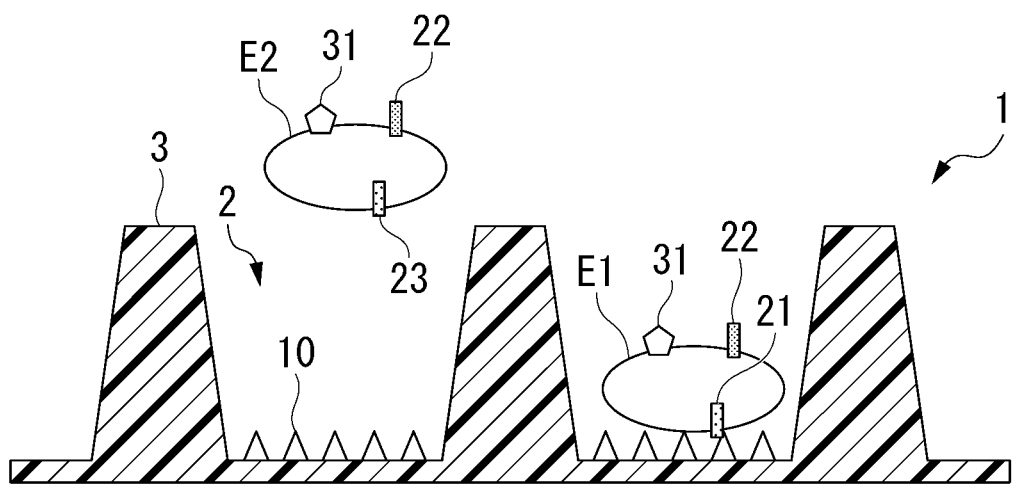
FIG. 1B is a view illustrating an example of Step (a) of the pancreatic cancer detection method according to one embodiment of the present invention.
Figure 1C:
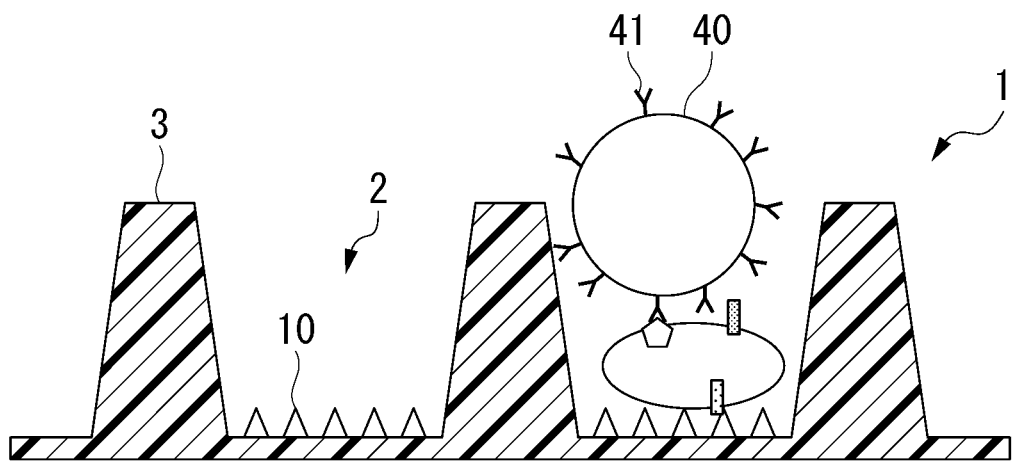
FIG. 1C is a view illustrating an example of Step (b) of the pancreatic cancer detection method according to one embodiment of the present invention.

A solid-phase carrier 1 of FIG. 1A is an example of a solid-phase carrier used for bringing extracellular vesicles into contact with lectins 10. The solid-phase carrier 1 has concave portions 2 and convex portions 3, and the lectins 10 are immobilized on the concave portions 2. If a body fluid sample derived from a subject is added to the solid-phase carrier 1, extracellular vesicles (E1, E2) in the body fluid sample can be brought into contact with the lectins 10 (Step (a): FIG. 1B).

The extracellular vesicle E1 has sugar chains 21 and 22, and the sugar chain 21 binds to the lectins 10 since it has a binding property with the lectins 10. On the other hand, the extracellular vesicle E2 has sugar chains 22 and 23, but the sugar chains do not bind to the lectins 10 since these do not have a binding property with the lectins 10.

Next, the amount of extracellular vesicles E1 bound to the lectins 10 is measured (Step (b): FIG. 1C). For example, antibodies 41 binding to pan-extracellular vesicle membrane proteins can be bound to the extracellular vesicles E1, and signals of the labels bound to the antibodies 41 can be detected to measure the amount of extracellular vesicles E1. In the example of FIG. 1C, an antibody 41 is immobilized on a solid-phase carrier particle 40, and a signal of the solid-phase carrier particle 40 is detected.

Next, the presence of pancreatic cancer in the subject is evaluated based on the measured amount of extracellular vesicles E1. For example, it is evaluated that pancreatic cancer is present in the subject in a case where the amount of extracellular vesicles E1 measured in Step (b) is larger than a measurement value in a body fluid sample from a healthy subject.

In the pancreatic cancer detection method of the present embodiment, pancreatic cancer is detected using the amount of extracellular vesicles binding to the lectins as an index as described above. Extracellular vesicles are vesicles released by cells. The size of extracellular vesicles is about 30 nm to 1 μm in diameter. Examples of extracellular vesicles include exosomes, apoptotic bodies, and microvesicles.

In the pancreatic cancer detection method of the present embodiment, extracellular vesicles used as indexes are preferably exosomes. Exosomes are membrane vesicles surrounded by a lipid bilayer membrane having a diameter of 50 to 150 nm, and intraluminal membrane vesicles germinating inward into the endosomal lumen are secreted in a body fluid from various cells including cancer cells.

Extracellular vesicles are secretions of cells and express various proteins derived from cells serving as a secretory source on surfaces of the extracellular vesicles. Sugar chains, which are one of the post-translational modifications of proteins, are present on all cell membranes and secretory proteins, and it is supposed that their structures change due to cell differentiation and canceration. Membrane proteins of extracellular vesicles are also subjected to sugar chain modification, and sugar chain structures differ depending on the cells serving as a secretory source. The pancreatic cancer detection method of the present embodiment is based on the finding that the amount of extracellular vesicles in a body fluid sample which have a binding property with specific lectins increases (or decreases) in an individual having pancreatic cancer compared to an individual not having pancreatic cancer.

[Step (a)]

In Step (a), extracellular vesicles in a body fluid sample derived from a subject are brought into contact with one or more kinds of lectins. Step (a) is performed in vitro.

The "body fluid sample derived from a subject" is a body fluid sample collected from a subject and a sample obtained by subjecting a body fluid sample collected from a subject to certain processing. The body fluid sample derived from a subject is not particularly limited as long as it contains extracellular vesicles. The method for processing the body fluid sample collected from a subject is not particularly limited, but examples thereof include removing cellular components (for example, centrifugal separation processing) and diluting with a buffer solution (such as PBS, PBS-T, physiological saline, or a Tris buffer solution).

The body fluid sample is not particularly limited as long as it contains extracellular vesicles. Since extracellular vesicles are stably present in most body fluids, most body fluids can be used. Examples of body fluid samples include blood, serum, plasma, saliva, urine, tears, sweat, milk, nasal mucus, semen, pleural fluid, gastrointestinal secretions, cerebrospinal fluid, interstitial fluid, and lymphatic fluid, but are not limited thereto. Extracellular vesicles are relatively stable even in a body fluid which has been collected from a subject and then preserved in a refrigerator or a freezer for a long period of time. For this reason, body fluid samples preserved for a long period of time after collection can also be used.

As a body fluid sample derived from a subject, serum or plasma is preferable and serum is more preferable.

The "subject" is an animal individual which is a target of pancreatic cancer detection. The subject is not particularly limited as long as it is an animal in which pancreatic cancer can develop, but examples thereof include humans or non-human mammals. Examples of non-human mammals include primates (such as monkeys, chimpanzees, and gorillas), rodents (such as mice, hamsters, and rats), rabbits, dogs, cats, cows, goats, sheep, and horses. Preferably, the subject is a human.

Lectins are proteins having a binding property with sugar chains. Lectins brought into contact with extracellular vesicles in a body fluid sample may be one or more kinds or may be two or more kinds. The type of lectin is not particularly limited but preferably includes at least one selected from the group consisting of DSA, STL, LEL, ACA, UDA, ABA, MAH, and TJA-1. As will be shown in examples to be described below, it has been confirmed that the amount of extracellular vesicles binding to such lectins significantly increases in pancreatic cancer patients compared to that of healthy subjects. Among the above, lectins preferably include at least one selected from the group consisting of ACA and ABA.

Lectins may be mutants of the above-described lectins as long as these have an ability to bind to sugar chains. A "mutant of a lectin" is a protein which consists of an amino acid sequence of the lectin in which one or more amino acids are mutated and has a sugar chain-binding property of the original lectin. The mutation of amino acids is at least one selected from the group consisting of substitution, addition, deletion, and insertion.

Examples of mutants of lectins include:

(1) a protein which consists of an amino acid sequence of an original lectin in which one or some amino acids are mutated and has a sugar chain-binding property of the original lectin; and (2) a protein which consists of an amino acid sequence having 80% or more sequence identity with respect to an amino acid sequence of an original lectin and has a sugar chain-binding property of the original lectin.

Examples of the "some" in (1) include 2 to 20, 2 to 15, 2 to 10, 2 to 5, 2 to 4, and 2 or 3. The sequence identity in (2) is preferably greater than or equal to 85%, more preferably greater than or equal to 90%, still more preferably greater than or equal to 95%, and particularly preferably greater than or equal to 96%, greater than or equal to 97%, greater than or equal to 98%, or greater than or equal to 99%. Two amino acid sequences are juxtaposed with gaps at insertion and deletion sites so that the largest number of corresponding amino acids coincides with each other, and the sequence identity of amino acid sequences is obtained as a ratio of matching amino acids to the entire amino acid sequences excluding the gaps in the obtained alignment. The sequence identity of amino acid sequences can be obtained using various well-known homology search software programs in the technical field. For example, the value of the sequence identity of amino acid sequences can be obtained through calculation based on alignment obtained using well-known homology search software BLASTP.

Examples of preferred mutants include mutants in which some amino acids constituting the original lectin are conservatively substituted. The "conservative substitution" is substitution with amino acids having similar biochemical properties. Examples of conservative substitution include: substitution between alanine, valine, leucine, and isoleucine having an aliphatic side chain; substitution between serine and threonine having a hydroxy group side chain; substitution between aspartic acid and glutamic acid having an acidic side chain; substitution between asparagine and glutamine having an amide group side chain; substitution between lysine and arginine having a basic side chain; and substitution between phenylalanine and tryptophan having an aromatic side chain.

A method for bringing extracellular vesicles in a body fluid sample into contact with one or more kinds of lectins is not particularly limited. For example, the solid-phase carrier 1 on which the lectins 10 are immobilized as shown in FIG. 1A may be used. The solid-phase carrier 1 of FIG. 1A has concave portions 2 and convex portions 3, and the lectins 10 are immobilized on the concave portions 2. In this case, as shown in FIG. 1B, extracellular vesicles (E1 and E2 in FIG. 1B) can be brought into contact with the lectins 10 by supplying a body fluid sample containing the extracellular vesicles to the solid-phase carrier 1. If the extracellular vesicles are brought into contact with the lectins 10, because the extracellular vesicle E1 has a sugar chain 21 having a binding property with the lectins 10, it binds to the lectins 10 through the sugar chain 21 and is captured in a concave portion 2. On the other hand, since the extracellular vesicle E2 has no sugar chain having a binding property with the lectins 10, it does not bind to the lectins 10. Accordingly, only the extracellular vesicle E1 having a binding property with the lectins 10 can be captured on the solid-phase carrier 1.

The material of the solid-phase carrier 1 is not particularly limited, but examples thereof include: resins such as polystyrene, polyolefin (such as polyethylene and polypropylene), cycloolefin polymers, and polycarbonates; and glass. The solid-phase carrier 1 may be a well plate which is surface-treated so that lectins can bind therewith, and the concave portion 2 may be a well of the well plate. Alternatively, the solid-phase carrier 1 may be one obtained by providing the concave portions 2 and the convex portions 3 on a surface-treated substrate.

Well-known methods can be performed as the method for immobilizing the lectins 10 on the solid-phase carrier 1. For example, the surface on which lectins are immobilized may be surface-treated so that proteins are physically adsorbed due to surface hydrophobic interactions or may be surface-treated so as to have an amino group, a carboxyl group, or the like. Alternatively, the lectins 10 may be immobilized on the concave portions 2 using an avidin-biotin bond.

In a case where two or more kinds of lectins are used as lectins to be brought into contact with extracellular vesicles, the contact with the extracellular vesicles is preferably performed for each type of lectin. For example, in the example of FIG. 1A, the lectins 10 immobilized on one solid-phase carrier 1 are one type of lectin, and the solid-phase carrier 1 is prepared for each type of lectin. Then, body fluid samples are each supplied to a plurality of solid-phase carriers 1, and extracellular vesicles in the body fluid samples are brought into contact with the lectins 10.

After the extracellular vesicles are brought into contact with the lectins 10, the solid-phase carriers 1 may be appropriately washed using a washing liquid. Extracellular vesicles that do not bind to the lectins 10 can be removed by washing the solid-phase carriers 1. The washing liquid is not particularly limited, but a washing liquid used for washing through ELISA or the like can be used. Examples of washing liquids include a buffer solution or one obtained by adding a surfactant such as Tween 20 to a buffer solution. Examples of washing liquids include, but are not limited to, PBS, PBS-T, a Tris buffer solution, an HEPES buffer solution, and pure water.

The method for bringing lectins into contact with extracellular vesicles in a body fluid sample is not limited to the method using the solid-phase carrier 1, and any methods well-known in the technical field can be used. For example, the contact between lectins and extracellular vesicles in a body fluid sample may be performed using magnetic beads or the like on which the lectins are immobilized. In this case, extracellular vesicles bound to the lectins can be collected by collecting the magnetic beads.

In addition, the contact between lectins and extracellular vesicles in a body fluid sample may be performed in a liquid phase by adding the lectins to the body fluid sample. In this case, the extracellular vesicles bound to the lectins can be collected using sugar chains specifically binding to lectins, a solid-phase carrier on which antibodies are immobilized, or the like. Here, "specifically binding" means having a high binding property with a target substance but having almost no binding property with other substances.

In addition, after extracellular vesicles are first captured by a solid-phase carrier using antibodies specifically binding to pan-extracellular vesicle membrane proteins, a solution containing lectins may be supplied on the solid-phase carrier to bring the extracellular vesicles into contact with the lectins. Here, the "pan-extracellular vesicle membrane proteins" are membrane proteins ubiquitously possessed by extracellular vesicles. The pan-extracellular vesicle membrane proteins may be membrane proteins ubiquitously possessed by all extracellular vesicles such as exosomes, apoptotic bodies, and microvesicles or may be membrane proteins generally expressed in any of exosomes, apoptotic bodies, and microvesicles. For example, the pan-extracellular vesicle membrane proteins can be membrane proteins ubiquitously possessed by exosomes (hereinafter, also referred to as "pan-exosome membrane proteins"). Being "ubiquitously possessed by extracellular vesicles" means being possessed by a wide variety of extracellular vesicles. Being "ubiquitously possessed by exosomes" means being possessed by a wide variety of exosomes. Examples of pan-exosome membrane proteins include CD9, CD63, and CD81.

In a case where lectins are not immobilized on the solid-phase carrier 1, the lectins may be labeled with labeled molecules. Fluorescent molecules or the like to be described below can be preferably used as the labeled molecules. If labeled lectins are used, extracellular vesicles binding to the lectins can be measured in Step (b) to be described below by detecting the labeled molecules used for labeling. Alternatively, lectins may be immobilized on the solid-phase carrier particle 40 to be described below. In this case, extracellular vesicles binding to lectins can be measured in Step (b) to be described below by detecting signals of the solid-phase carrier particles 40 using an extracellular vesicle-measuring instrument or the like.

[Step (b)]

In Step (b), the amount of the extracellular vesicles bound to the one or more kinds of lectins after Step (a) is measured. Step (b) is a step performed in vitro.

The amount of extracellular vesicles bound to the lectins may be measured using the number of extracellular vesicles, the amount of proteins specifically expressed in extracellular vesicles, or the volume of extracellular vesicles.

The amount of extracellular vesicles bound to the lectins (hereinafter, also referred to as lectin-specific extracellular vesicles") can be measured using, for example, pan-extracellular vesicle membrane proteins expressed by extracellular vesicles. Such a method is not particularly limited, and methods usually used for detecting proteins can be used. For example, the extracellular vesicles E1 bound to the lectins 10 are measured using the solid-phase carrier particles 40 on which the antibodies 41 binding to pan-extracellular vesicle membrane proteins are immobilized. The antibodies 41 are antibodies specifically binding to pan-extracellular vesicle membrane proteins 31, and if a solution containing the antibodies 41 is supplied on the solid-phase carrier 1, it is supplied to the extracellular vesicles E1 captured in the concave portions 2. For this reason, the extracellular vesicles E1 can be measured by measuring the solid-phase carrier particles 40.

The material of the solid-phase carrier particles 40 is not particularly limited, but examples thereof include: resins such as polystyrene and glycidyl methacrylate; and magnetic beads. The solid-phase carrier particles 40 can be measured by, for example, irradiating the solid-phase carrier 1 with a laser beam and analyzing reflected light from the solid-phase carrier 1. The particle size of the solid-phase carrier particles 40 is not particularly limited. The particle size of the solid-phase carrier particles 40 can be, for example, 1,000 nm or less. The particle size of the solid-phase carrier particles 40 can be, for example, 1 to 500 nm, 10 to 300 nm, or 10 to 200 nm. The solid-phase carrier particles 40 may be nanoparticles having a particle size with nano-order (1 to 1,000 nm).

A pan-exosome membrane protein can be selected as the pan-extracellular vesicle membrane protein 31 in a case where measurement targets are exosomes. Examples of pan-exosome membrane proteins include CD9, CD63, and CD81.

The antibodies 41 can be produced through a well-known antibody production method (such as a hybridoma method or a phase display method) using pan-extracellular vesicle membrane proteins as antigens. The antibodies 41 may be polyclonal antibodies or may be monoclonal antibodies. Animals from which the antibodies 41 are derived are not particularly limited, but animals generally used for producing antibodies can be used. For example, goat antibodies, mouse antibodies, rat antibodies, rabbit antibodies, monkey antibodies, and human antibodies can be used.

It is unnecessary for the antibodies 41 to be intact antibodies, and the antibodies 41 may be antigen-binding fragments. The "antigen-binding fragments" are polypeptides which contain a part of an antibody and maintain an antigen-binding property of the original antibody. Examples of antigen-binding fragments include scFv, Fab, F(ab')2, and Fv. In addition, the antibodies 41 may be modified antibodies such as chimeric antibodies.

Immobilization of the antibodies 41 on the solid-phase carrier particles 40 can be performed through a well-known method. For example, the same methods as those exemplified for immobilizing the lectins 10 on the solid-phase carrier 1 can be used.

In a case where the solid-phase carrier particle 40 on which the antibodies 41 are immobilized is used, a commercially available extracellular vesicle-measuring instrument (for example, an exosome-measuring instrument) or the like can be used for detecting the solid-phase carrier particle 40. The "extracellular vesicle-measuring instrument" is a device that can count extracellular vesicles by detecting a signal of a signal substance directly or indirectly bound to extracellular vesicles. The solid-phase carrier particle 40 functions as the signal substance. For example, ExoCounter (registered trademark) (JVC Kenwood) or the like can be used as a commercially available extracellular vesicle-measuring instrument. In a case of using an extracellular vesicle-measuring instrument, ones which will be described in detail in [Pancreatic Cancer Detection Kit] below can be used as the solid-phase carrier 1 and the solid-phase carrier particle 40.

Measurement of lectin-specific extracellular vesicles (extracellular vesicles E1) may be performed using labeled molecules instead of the solid-phase carrier particles 40. For example, the extracellular vesicles E1 can be measured by labeling the antibodies 41 with labeled molecules and measuring the signals of the labeled molecules. Labeled molecules generally used in ELISA or the like can be used as the labeled molecules without particular limitation. Examples of labeled substances include: enzyme labels such as peroxidase (for example, horseradish peroxidase) and alkaline phosphatase; fluorescent labels such as carboxyfluorescein (FAM), 6-carboxy-4',5'-dichloro-2',7'-dimethoxyfluorescein (JOE), fluorescein isothiocyanate (FITC), tetrachlorofluorescein (TET), 5'-hexachloro-fluorescein-CE phosphoramidite (HEX), Cy3, Cy5, Alexa568, and Alexa647; radioisotope labels such as iodine 125; electrochemiluminescence labels such as ruthenium complexes; biotin; and metal nanoparticles.

Detection of a signal of a labeled molecule can be performed through a well-known method depending on a labeled molecule to be used. For example, by binding labeled antibodies specifically binding to pan-extracellular vesicle membrane proteins to lectin-specific extracellular vesicles and measuring signals of labeled molecules, the amount of pan-extracellular vesicle membrane proteins expressed by the lectin-specific extracellular vesicles can be measured. The amount of the pan-extracellular vesicle membrane proteins can be regarded as an amount of lectin-specific extracellular vesicles. Furthermore, the amount of exosome may be measured by measuring the amount of protein such as CD9, CD63, or CD81, each of which is regarded as a pan-exosome membrane protein.

After reacting the antibodies 41 with the solid-phase carrier 1, the solid-phase carrier 1 may be appropriately washed with a washing liquid before detecting the solid-phase carrier particles 40 or the labeled molecules. Antibodies 41 that do not bind to the extracellular vesicles E1 can be removed by washing the solid-phase carrier 1. The washing liquid is not particularly limited, but a washing liquid used for washing through ELISA or the like can be used. Examples of washing liquids include a buffer solution or one obtained by adding a surfactant such as Tween 20 to a buffer solution. Examples of washing liquids include, but are not limited to, PBS, PBS-T, a Tris buffer solution, an HEPES buffer solution, and pure water.

In a case where labeled lectins which have not been immobilized on the solid-phase carrier 1 are used in Step (a), extracellular vesicles bound to the lectins can be measured by measuring signals of labeled molecules used for the labeling. For example, in a case where fluorescent molecules are used as labeled molecules, extracellular vesicles bound to lectins can be measured through flow cytometry or the like. In addition, in a case where extracellular vesicles are captured on a solid-phase carrier using antibodies specifically binding to pan-extracellular vesicle membrane proteins immobilized on the solid-phase carrier and the lectins immobilized on the solid-phase carrier particles are brought into contact with the extracellular vesicles in Step (a), signals of the solid-phase carrier particles can be detected using an extracellular vesicle-measuring instrument or the like to measure the extracellular vesicles bound to the lectins.

Specific examples of the methods for carrying out Steps (a) and (b) will be shown below, but the present invention is not limited thereto.

(1) A method for measuring the amount of extracellular vesicles bound to the lectins with an extracellular vesicle-measuring instrument using a solid-phase carrier on which the lectins are immobilized and solid-phase carrier particles on which antibodies specifically binding to pan-extracellular vesicle membrane proteins are immobilized.

(2) A method for measuring the amount of extracellular vesicles bound to the lectins through an immunological measurement method such as sandwich ELISA using a solid-phase carrier on which the lectins are immobilized and antibodies which specifically bind to pan-extracellular vesicle membrane proteins and which are labeled with labeled molecules.

(3) A method for measuring the amount of extracellular vesicles bound to the lectins with an extracellular vesicle measuring instrument using a solid-phase carrier on which antibodies which specifically bind to pan-extracellular vesicle membrane proteins are immobilized and solid-phase carrier particles on which the lectins are immobilized.

(4) A method for measuring the amount of extracellular vesicles bound to the lectins through an immunological measurement method such as sandwich ELISA using a solid-phase carrier on which antibodies which specifically bind to pan-extracellular vesicle membrane proteins are immobilized and the lectins which is labeled with labeled molecules.

(5) A method for measuring the amount of extracellular vesicles bound to the lectins through flow cytometry using the lectins which is labeled with labeled molecules.

(6) A method for collecting extracellular vesicles bound to the lectins using magnetic beads on which the lectins are immobilized to measure the amount of extracellular vesicles bound to the lectins through flow cytometry using antibodies which specifically bind to pan-extracellular vesicle membrane proteins and which are labeled with labeled molecules.

(7) A method for collecting extracellular vesicles using magnetic beads on which antibodies which specifically bind to pan-extracellular vesicle membrane proteins are immobilized to measure the amount of extracellular vesicles bound to the lectins through flow cytometry using the lectins which are labeled with labeled molecules.

Examples of more specific methods for carrying out Steps (a) and (b) include the following methods.

Exosomes bound to the lectins are collected using a solid-phase carrier on which the lectins are immobilized, and the amount of pan-exosome membrane proteins in the exosomes collected using the lectins is measured through an immunological measurement method such as ELISA using the pan-exosome membrane proteins as a target.

Alternatively, pan-exosome membrane proteins on exosomes captured on a solid-phase carrier on which the lectins are immobilized are labeled with fluorescence-labeled antibodies, and the amount thereof is measured through flow cytometer.

[Step (c)]

In Step (c), the presence of pancreatic cancer in the subject is evaluated based on the amount of the extracellular vesicles measured in Step (b).

The amount of extracellular vesicles (lectin-specific extracellular vesicles) measured in Step (b) differs between a case where a subject from which a body fluid sample is derived has pancreatic cancer and a case where the subject does not have pancreatic cancer. For this reason, the presence of pancreatic cancer in the subject can be evaluated based on the amount of the extracellular vesicles measured in Step (b).

More specifically, it is possible to determine that pancreatic cancer is present in the subject in a case where the amount of the extracellular vesicles measured in Step (b) is larger than or smaller than the amount of lectin-specific extracellular vesicles measured in a non-pancreatic cancer body fluid sample. The "non-pancreatic cancer body fluid sample" is a body fluid sample derived from an individual known to not have pancreatic cancer or very unlikely to have pancreatic cancer. For example, body fluid samples derived from individuals who have not been diagnosed with pancreatic cancer through various kinds of image diagnosis such as abdominal ultrasonography, a CT examination, a MRI examination, magnetic resonance cholangiopancreatography (MRCP), endoscopic ultrasonography (EUS), endoscopic retrograde cholangiopancreatography (ERCP), and positron emission tomography (PET) can be used as the "non-pancreatic cancer body fluid sample". The non-pancreatic cancer body fluid sample may be a body fluid sample from a so-called healthy subject. In addition, it may be a body fluid sample from a patient with cancer other than pancreatic cancer.

A body fluid sample of the same kind as a body fluid sample from a subject to be evaluated is used as the non-pancreatic cancer body fluid sample. For example, in a case where a body fluid sample to be evaluated is serum, serum is also used as a non-pancreatic cancer body fluid sample. Extracellular vesicles binding to lectins in a non-pancreatic cancer body fluid sample can be measured through the same method as in Steps (a) and (b) described above. It is preferable to measure extracellular vesicles binding to the lectins in a non-pancreatic cancer body fluid sample through the same method as in a body fluid sample from a subject except that the non-pancreatic cancer body fluid sample is used as a body fluid sample.

In Step (c), the amount of lectin-specific extracellular vesicles in the non-pancreatic cancer body fluid sample used for comparison may be a measurement value in a body fluid sample from an individual, or may be an average value or median value of measurement values in body fluid samples from a plurality of individuals. Alternatively, the amount of lectin-specific extracellular vesicles in a non-pancreatic cancer body fluid sample may be calculated by subjecting measurement values of lectin-specific extracellular vesicles from a plurality of individuals to statistical processing such as exclusion of outliers. In addition, the amount of lectin-specific extracellular vesicles in a non-pancreatic cancer body fluid sample may be a cutoff value determined based on the amount of lectin-specific extracellular vesicles in a non-pancreatic cancer body fluid sample and a pancreatic cancer body fluid sample measured in advance. The cutoff value can be set based on, for example, the ROC curve. The ROC curve can be created by calculating the sensitivity and specificity at each cutoff value from the amount of lectin-specific extracellular vesicles in a non-pancreatic cancer body fluid sample and a pancreatic cancer body fluid sample measured in advance and plotting the pseudopositive rate (1-specificity) on the horizontal axis and the sensitivity on the longitudinal axis of coordinates. The cutoff values are preferably set so that the sensitivity is high and the pseudopositive rate is low.

The measurement of lectin-specific extracellular vesicles in a non-pancreatic cancer body fluid sample may be performed simultaneously to measurement in a body fluid sample from a subject or at different times. For example, the amount of lectin-specific extracellular vesicles in a non-pancreatic cancer body fluid sample may be measured in advance before measuring a body fluid sample from a subject. In addition, in a case of measuring the amount of lectin-specific extracellular vesicles in a plurality of non-pancreatic cancer body fluid samples, the measurement in the plurality of non-pancreatic cancer body fluid samples may be performed simultaneously or at different times. For example, measurement values may be accumulated by measuring the amount of lectin-specific extracellular vesicles in a plurality of non-pancreatic cancer body fluid samples during an arbitrary period, and a calculated value obtained by subjecting the accumulated measurement values to statistical processing may be used as an amount of lectin-specific extracellular vesicles in a non-pancreatic cancer body fluid sample.

In a case where the lectins used in Step (a) are selected from the group consisting of DSA, STL, LEL, ACA, UDA, ABA, MAH, and TJA-1, if the amount of the extracellular vesicles measured in Step (b) is larger than that measured in a non-pancreatic cancer body fluid sample, it is possible to evaluate that pancreatic cancer is present in the subject. For example, in a case where the amount of the extracellular vesicles measured in Step (b) is 1.2 times or more, preferably 1.5 times or more, and more preferably 2 times or more of the amount measured in a non-pancreatic cancer body fluid sample, it is possible to evaluate that pancreatic cancer is present in the subject. On the other hand, in a case where the amount of the extracellular vesicles measured in Step (b) is about the same as or lower than that measured in a non-pancreatic cancer body fluid sample, it is possible to evaluate that there is a low possibility that pancreatic cancer may be present in the subject. The "about the same as the amount measured in a non-pancreatic cancer body fluid sample" is, for example, less than 1.2 times, preferably 1.1 times or less, and more preferably 1 time or less of the amount measured in a non-pancreatic cancer body fluid sample.

In a case where two or more kinds of lectins are used in Step (a), a measurement value of an extracellular vesicle binding to each kind of lectin can be obtained in Step (b). In this case, these measurement values may be combined to evaluate the presence of pancreatic cancer in the subject in Step (c). For example, in a case where all of the measurement values in two or more kinds of lectins are larger than a measurement value in a non-pancreatic cancer body fluid sample, it is possible to evaluate that pancreatic cancer is present in the subject. In this case, the greater the number of kinds of lectins used in Step (a), the higher the accuracy of the evaluation that pancreatic cancer is present in the subject. Alternatively, in a case where at least one of the measurement values in two or more kinds of lectins is larger than a measurement value in a non-pancreatic cancer body fluid sample, it is possible to evaluate that pancreatic cancer is present in the subject. In this case, it is possible to broadly capture subjects who are likely to have pancreatic cancer. Alternatively, in a case where a specific proportion (for example, the majority) of measurement values in two or more kinds of lectins is larger than a measurement value in a non-pancreatic cancer body fluid sample, it may be evaluated that pancreatic cancer is present in the subject.

The stage of pancreatic cancer whose presence in a subject is evaluated in Step (c) is not particularly limited. Pancreatic cancer in any of Stages I to IV can be detected in the pancreatic cancer detection method of the present embodiment. Since early-stage pancreatic cancer in Stage I can also be detected in the pancreatic cancer detection method of the present embodiment, the method can be suitably used for screening early-stage pancreatic cancer.

In addition, pancreatic cancer whose presence in a subject is evaluated in Step (c) may be pancreatic cancer that has recurred after surgery. If pancreatic cancer is resected through surgery, the amount of lectin-specific extracellular vesicles decreases to the same degree as that of a non-pancreatic cancer body fluid sample. However, it is assumed that, if pancreatic cancer has recurred, the amount of lectin-specific extracellular vesicles increases again. For this reason, the pancreatic cancer detection method of the present embodiment can be suitably used as a method for monitoring the therapeutic effect of pancreatic cancer.

[Optional Steps]

The detection method of the present embodiment may include optional steps in addition to Steps (a) to (c) described above. Examples of optional steps include a step (blocking step) of blocking a solid-phase carrier 1 before Step (a) and a step (treatment step) of treating pancreatic cancer after Step (c).

<Blocking Step>

The solid-phase carrier 1 on which the lectins 10 are immobilized may be blocked before Step (a). By performing the blocking treatment, it is possible to suppress extracellular vesicles which do not bind to the lectins 10 from nonspecifically binding to the solid-phase carrier 1.

The blocking treatment can be performed using a well-known blocking liquid. Blocking liquids, such as ones that are usually used in ELISA or the like, can be used without particular limitation. Examples of blocking liquids include a buffer solution containing about 1% to 5% skim milk or bovine serum albumin (BSA). The buffer solution for a blocking liquid is not particularly limited, but examples thereof include PBS, PBS-T, a Tris buffer solution, and a HEPES buffer solution.

<Treatment Step>

In a case where it is evaluated in Step (c) that pancreatic cancer is present in the subject, a step of treating pancreatic cancer may be performed.

Accordingly, the present invention also provides a pancreatic cancer treatment method: Step (a) of bringing extracellular vesicles, which are in a body fluid sample derived from a subject, into contact with one or more kinds of lectins; Step (b) of measuring amount of the extracellular vesicles bound to the one or more kinds of lectins after Step (a); Step (c) of evaluating (or determining) the presence of pancreatic cancer in the subject based on the amount of the extracellular vesicles measured in Step (b); and Step (d) of treating the pancreatic cancer in a case where it is evaluated (or determined) in Step (c) that pancreatic cancer is present in the subject. Step (c) may be a step of determining whether the subject has pancreatic cancer based on the amount of the extracellular vesicles measured in Step (b). Step (c) may be a step of identifying the subject having pancreatic cancer based on the amount of the extracellular vesicles measured in Step (b). Step (c) may include identifying the subject in which the amount of the extracellular vesicles measured in (b) is larger than that of extracellular vesicles binding to the one or more kinds of lectins measured using a body fluid sample from a subject known to not have pancreatic cancer, as the subject having pancreatic cancer. Step (d) may be a step of treating the pancreatic cancer in the subject who is determined that pancreatic cancer is present in the subject in Step (c). Step (d) may be a step of treating the pancreatic cancer in the subject who is determined to have pancreatic cancer in (c). Step (d) may be a step of treating the pancreatic cancer in the subject having pancreatic cancer who is identified in (c).

It can also be said that Step (c) may be a step of diagnosing whether the subject is suffering from pancreatic cancer based on the amount of the extracellular vesicles measured in Step (b).

The pancreatic cancer treatment method is not particularly limited, and methods usually used for treating pancreatic cancer can be used. Examples thereof include surgical resection of pancreatic cancer, radiotherapy, and administration of anticancer drugs (such as gemcitabine, TS-1, and erlotinib). Step (d) may be a step of performing at least one treatment selected from the group consisting of surgical resection of pancreatic cancer, radiotherapy, and administration of anticancer drugs in the subject having pancreatic cancer identified in Step (c).

In addition, a confirmed diagnosis of pancreatic cancer may be performed through various kinds of image diagnosis such as abdominal ultrasonography, a CT examination, a MRI examination, magnetic resonance cholangiopancreatography (MRCP), endoscopic ultrasonography (EUS), endoscopic retrograde cholangiopancreatography (ERCP), and positron emission tomography (PET), and cytodiagnosis or histological diagnosis before treating pancreatic cancer after Step (c). Treatment of pancreatic cancer may be carried out on subjects who have been confirmed to have pancreatic cancer through these methods.

According to the pancreatic cancer detection method of the present embodiment, it is possible to detect pancreatic cancer in vitro using a body fluid sample from a subject. Therefore, it is possible to easily detect pancreatic cancer through a non-invasive method. In addition, according to the pancreatic cancer detection method of the present embodiment, it is possible to detect pancreatic cancer at an early stage. In addition, it is possible to monitor the effect of treating pancreatic cancer.

(Pancreatic Cancer Detection Kit)

In one embodiment, the present invention provides a pancreatic cancer detection kit including: a solid-phase carrier on which one or more kinds of lectins are immobilized; and an antibody specifically binding to a pan-extracellular vesicle membrane protein or an antigen-binding fragment thereof.

[Solid-Phase Carrier on which One or More Kinds of Lectins are Immobilized]

The same one (for example, the solid-phase carrier 1 shown in FIG. 1A) as that described in [Step (a)] of (Pancreatic Cancer Detection Method) described above can be used as a solid-phase carrier on which one or more kinds of lectins are immobilized. In a case where two or more kinds of lectins are used, one kind of lectin is preferably immobilized on one solid-phase carrier. Alternatively, one solid-phase carrier may be partitioned into a number of kinds of lectins to immobilize one kind of lectin in one section. Lectins to be immobilized on a solid-phase carrier preferably include at least one selected from the group consisting of DSA, STL, LEL, ACA, UDA, ABA, MAH, and TJA-1 and more preferably include at least one selected from the group consisting of ACA and ABA.

[Antibody Specifically Binding to Pan-Extracellular Vesicle Membrane Protein or Antigen-Binding Fragment Thereof]

The same ones as those described in [Step (b)] of (Pancreatic Cancer Detection Method) described above can be used as antibodies specifically binding to pan-extracellular vesicle membrane proteins or antigen-binding fragments thereof. The pan-extracellular vesicle membrane protein may be a pan-exosome membrane protein. Examples of pan-exosome membrane proteins include CD9, CD63, and CD81.

The antibodies specifically binding to pan-extracellular vesicle membrane proteins or the antigen-binding fragments thereof may be immobilized on a solid-phase carrier particle, or may be labeled with labeled molecules. Examples of solid-phase carrier particles and labeled molecules include the same ones as those exemplified above.

<Pancreatic Cancer Detection Kit Used in Extracellular Vesicle Counter>

The pancreatic cancer detection kit of the present embodiment may be used in the extracellular vesicle-measuring instrument. A commercially available extracellular vesicle counter can be used, and examples thereof include ExoCounter (registered trademark) (JVC Kenwood). In the case where the pancreatic cancer detection kit is used in the extracellular vesicle-measuring instrument, a solid-phase carrier on which one or more kinds of lectins are immobilized may be included in the extracellular vesicle capture unit used in the extracellular vesicle counter. In addition, those immobilized on solid-phase carrier particles can be used as the antibodies specifically binding to pan-extracellular vesicle membrane proteins or the antigen-binding fragments thereof.

<<Extracellular Vesicle Capture Unit>>

An extracellular vesicle capture unit corresponding to an extracellular vesicle counter to be used can be used. Examples of solid-phase carriers included in an extracellular vesicle capture unit include those having the form of the solid-phase carrier 1 in FIG. 1A. Hereinafter, an example of an extracellular vesicle capture unit including the solid-phase carrier 1 will be described with reference to FIGS. 2A to 2C and FIGS. 3A and 3B.

Figure 2A:
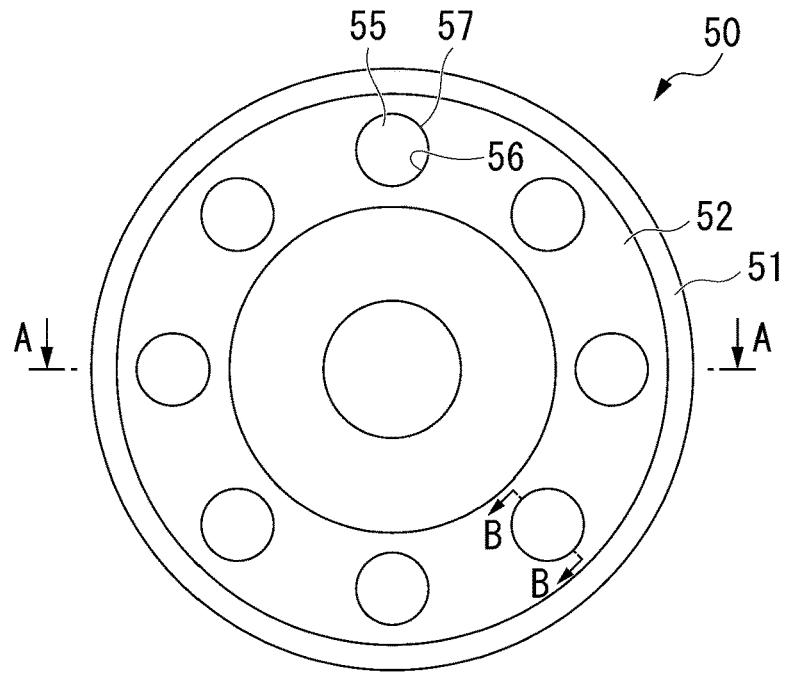
FIG. 2A is a schematic diagram illustrating an example of an extracellular vesicle capture unit set in an extracellular vesicle counter.
Figure 2B:
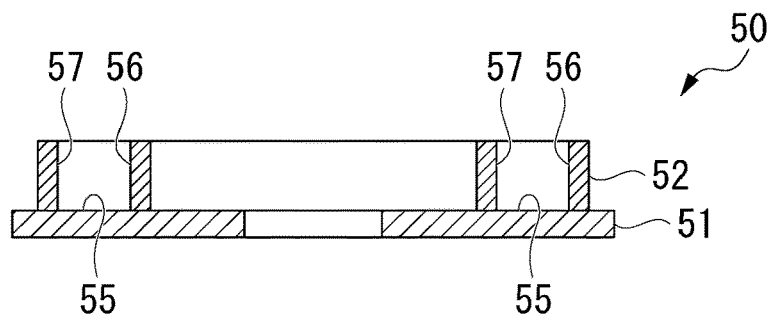
FIG. 2B is a schematic cross-sectional view of the extracellular vesicle capture unit taken along cut line A-A of FIG. 2A.
Figure 2C:
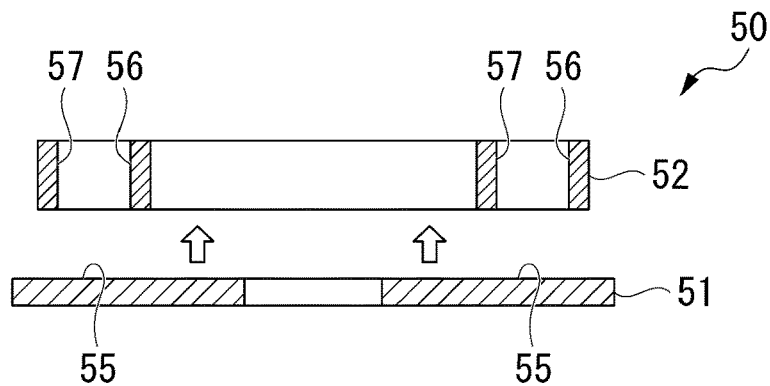
FIG. 2C is a schematic cross-sectional view illustrating that a cartridge 52 of the extracellular vesicle capture unit of FIG. 2A is removable.
Figure 3A:
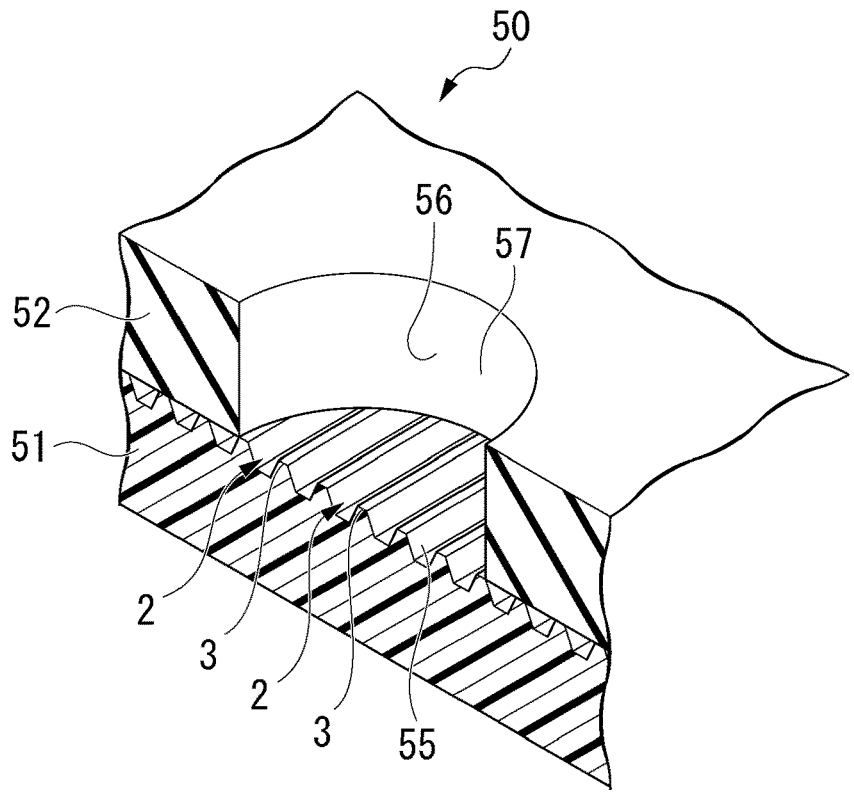
FIG. 3A is a schematic cross-sectional view of the extracellular vesicle capture unit taken along cut line B-B of FIG. 2A.

FIG. 2A is a schematic top view of an extracellular vesicle capture unit 50. FIG. 2B is a schematic cross-sectional view taken along cut line A-A of FIG. 2A. FIG. 2C is a schematic cross-sectional view illustrating that a cartridge 52 is removable from a substrate 51. FIG. 3A is a partially enlarged perspective view taken along cut line B-B of FIG. 2A.

As shown in FIG. 2A, the extracellular vesicle capture unit 50 includes the substrate 51 and the cartridge 52.

The substrate 51 has a disk shape equivalent to that of an optical disk such as a Blu-ray disk (BD), DVD, or a compact disk (CD), for example. The substrate 51 is made of, for example, a resin material such as a polycarbonate resin or a cycloolefin polymer generally used in optical disks.

As shown in FIG. 3A, a track region 55 in which convex portions 3 and concave portions 2 are alternately arranged in the radial direction is formed on the surface of the substrate 51. The convex portions 3 and the concave portions 2 are formed in a spiral shape from the inner circumferential portion to the outer circumferential portion. The convex portions 3 correspond to lands of an optical disk. The concave portions 2 correspond to grooves of an optical disk.

The substrate 51 corresponds to the solid-phase carrier 1 of FIG. 1A, and the convex portions 3 and the concave portions 2 formed in the substrate 51 respectively correspond to the convex portions 3 and the concave portions 2 of FIG. 1A. Lectins 10 are immobilized on at least the concave portions 2 in the track region 55 in which the concave portions 2 and the convex portions 3 are formed in the substrate 51.

As shown in FIG. 2A, the cartridge 52 has a ring shape. In the cartridge 52, a plurality of cylindrical through-holes 56 are formed in the circumferential direction.

As shown in FIGS. 2B and 3A, the extracellular vesicle capture unit 50 has a plurality of wells 57 formed by the through-holes 56 of the cartridge 52 and the track region 55 of the substrate 51. That is, the inner circumferential surface of the through-holes 56 constitutes the inner peripheral surface of the wells 57, and the track region 55 of the substrate 51 constitutes the bottom surface of the wells 57. The wells 57 are containers for storing sample solutions. In addition, if packing made of an elastically deformable material such as silicone rubber is placed between a through-hole 56 and the substrate 51, the possibility of a solution leaking can be reduced, which is favorable.

As shown in FIG. 2C, the cartridge 52 is detachable from the substrate 51. Detection of extracellular vesicles after capture thereof is performed in the substrate 51 after removing the cartridge 52 from the substrate 51.

In the extracellular vesicle capture unit 50, the contact between extracellular vesicles in a body fluid sample and the lectins 10 immobilized on the track region 55 in Step (a) can be performed by placing the body fluid sample in the wells 57. In addition, in a case where antibodies 41 specifically binding to pan-extracellular vesicle membrane proteins are used in Step (b), reactions between the antibodies 41 and extracellular vesicles E1 bound to the lectins 10 can be caused by placing a solution containing the antibodies 41 in the wells 57. In addition, even in a case of performing a washing treatment, a blocking treatment, or the like, these can be performed by placing a washing liquid, a blocking liquid, or the like in the wells 57. Before placing a solution for each treatment in the wells 57, a solution used in the previous treatment is preferably removed from the wells 57.

<<Solid-Phase Carrier Particles>>

Solid-phase carrier particles corresponding to an extracellular vesicle counter to be used can be used. Examples of solid-phase carrier particles include: resin particles such as polystyrene and glycidyl methacrylate; and magnetic beads. Antibodies specifically binding to pan-extracellular vesicle membrane proteins are immobilized on solid-phase carrier particles. Examples of solid-phase carrier particles include the solid-phase carrier particle 40 on which the antibodies 41 in FIG. 1C are immobilized.

Next, the relationship between the dimensions of the concave portions 2 and the convex portions 3 formed on the substrate 51 of the extracellular vesicle capture unit 50, the dimension of the solid-phase carrier particles, and the average particle diameter of the extracellular vesicles will be described.

Figure 3B:
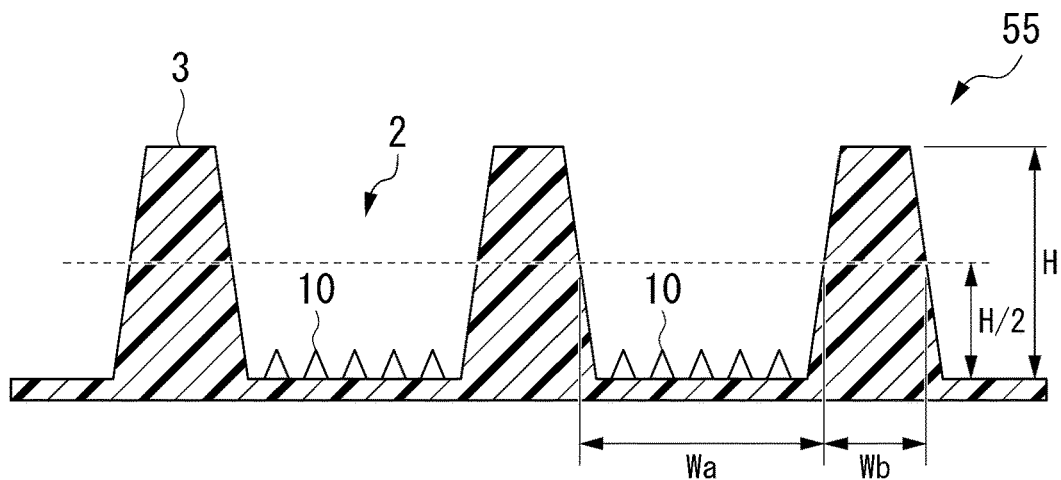
FIG. 3B is an enlarged cross-sectional view illustrating the dimensional shapes of concave portions and convex portions of the extracellular vesicle capture unit of FIG. 2A.

FIG. 3B is an enlarged cross-sectional view illustrating the dimensional shapes of the concave portions 2 and convex portions 3 formed in the track region 55 of the substrate 51. The depth of a concave portion 2 (the height of a convex portion 3) is set to H, the width of a concave portion 2 is set to Wa, and the width of a convex portion 3 is set to Wb. The width Wa and the width Wb are widths at the position of H/2 indicated by the dotted line.

The width Wb of a convex portion 3 is preferably smaller than an average particle diameter Ra of extracellular vesicles as shown in Inequation (1) described below. By satisfying Inequation (1) described below, it is difficult for extracellular vesicles to be positioned on the convex portions 3.

$$Wb<Ra \tag{1}$$

As shown in Inequation (2) described below, the width Wa of a concave portion 2 is preferably larger than the average particle diameter Ra of extracellular vesicles and smaller than 4 times the average particle diameter Ra. By satisfying Inequation (2) described below, extracellular vesicles are likely to be captured in the concave portions 2.

$$Ra<Wa<4\times Ra \tag{2}$$

Extracellular vesicles captured in the concave portions 2 are generally deformed from a spherical shape in a direction of expanding the contact area. Assuming that spherical extracellular vesicles are deformed into ellipsoids while maintaining their volume, in a case where the diameters of the spheres change by 50%, the diameter of a contact site with a concave portion 2 which is the major axis of a spheroid is increased by about 40%. Furthermore, in reality, extracellular vesicles are deformed in a direction in which the area of the contact site is larger than that of the shape of the spheroid. Therefore, the diameter of the contact site is increased by 50% or more, and in some cases, 100% or more of the diameter of the original spherical shape. Accordingly, Wa<4×Ra of Inequation (2) described above is preferably specified.

In addition, the width Wa of a concave portion 2, the width Wb of a convex portion 3, and the particle diameter Rc of a solid-phase carrier particle preferably satisfy Inequation (3) described below.

$$Wb<Rc<Wa<2\times Rc \tag{3}$$

By satisfying Wb<Rc of Inequation (3) described above, it is difficult for a solid-phase carrier particle to be positioned on the convex portion 3. By satisfying Rc<Wa of Inequation (3) described above, a solid-phase carrier particle is likely to be placed in the concave portion 2. By satisfying Wa<2×Rc of Inequation (3), it is difficult for two or more solid-phase carrier particles to be placed at the same time in the width direction of the concave portion 2. Therefore, the quantitative relationship between extracellular vesicles and the solid-phase carrier particles can be brought close to 1:1.

As shown in Inequation (4) described below, the particle diameter Rc of a solid-phase carrier particle is preferably larger than the average particle diameter Ra of extracellular vesicles.

$$Ra<Rc \tag{4}$$

By satisfying Inequation (4) described above, it is difficult for a plurality of solid-phase carriers to bind to extracellular vesicles immobilized on the concave portions 2. Therefore, the quantitative relationship between the extracellular vesicles and the solid-phase carrier particles can be brought close to 1:1. By satisfying Inequation (4), the probability that the extracellular vesicles and the solid-phase carrier particles reactively meet increases, and as a result, the yield of the reaction can be improved.

As shown in Inequation (5) described below, the depth H of a concave portion 2 is preferably larger than ⅛ times the sum of the average particle diameter Ra of the extracellular vesicles and the particle diameter Rc of a solid-phase carrier particle.

$$(Ra+Rc)/8<H \tag{5}$$

By satisfying Inequation (5) described above, extracellular vesicles are likely to be captured in the concave portions 2. In addition, since nonspecific adsorption of solid-phase carrier particles on the convex portions 3 is likely to occur, the solid-phase carrier particles are likely to bind to extracellular vesicles captured in the concave portions 2.

The depth H of a concave portion 2 more preferably satisfies Inequation (6).

$$(Ra+Rc)/6 < H \quad (6)$$

The concave portions 2, the convex portions 3, and the solid-phase carrier particles preferably satisfy all of Inequation (1) to Inequation (5) (or to Inequation (6)), but may only satisfy some of the inequations.

[Optional Components]

The pancreatic cancer detection kit of the present embodiment may include an optional component in addition to the above-described configuration. Examples of optional components include reagents (for example, diluted solution) for processing a body fluid sample, various reagents such as a washing liquid, a blocking liquid, and a buffer solution, and those in the instruction manual.

The pancreatic cancer detection kit may include detection reagents for detecting labeled molecules in a case where antibodies specifically binding to pan-extracellular vesicle membrane proteins or antigen-binding fragments thereof are labeled with labeled molecules. Well-known detection reagents can be used depending on the type of label. Furthermore, the pancreatic cancer detection kit of the present embodiment may include standard reagents. The standard reagents are reagents for creating calibration curves of lectin-specific extracellular vesicles. Standard reagents containing sugar chains to which lectins immobilized on a solid-phase carrier bind can be used, for example.

The pancreatic cancer detection kit of the present embodiment can be used for the pancreatic cancer detection method of the above-described embodiment.

(Other Aspects)

The present invention can also include the following aspects.

(1) A pancreatic cancer diagnosis method including: Step (a) of bringing extracellular vesicles, which are in a body fluid sample derived from a subject, into contact with one or more kinds of lectins in vitro; Step (b) of measuring an amount of the extracellular vesicles bound to the one or more kinds of lectins after Step (a); and Step (c) of evaluating the presence of pancreatic cancer in the subject based on the amount of the extracellular vesicles measured in Step (b).

(2) A method for specifying a body fluid sample derived from a subject with pancreatic cancer, the method including: Step (a) of bringing extracellular vesicles, which are in a body fluid sample derived from a subject, into contact with one or more kinds of lectins in vitro; Step (b) of measuring an amount of the extracellular vesicles bound to the one or more kinds of lectins after Step (a); and Step (c) of evaluating the presence of pancreatic cancer in the subject based on the amount of the extracellular vesicles measured in Step (b).

(3) A method for collecting data for diagnosing pancreatic cancer, the method including: Step (a) of bringing extracellular vesicles, which are in a body fluid sample derived from a subject, into contact with one or more kinds of lectins in vitro; Step (b) of measuring an amount of the extracellular vesicles bound to the one or more kinds of lectins after Step (a); and Step (c) of evaluating the presence of pancreatic cancer in the subject based on the amount of the extracellular vesicles measured in Step (b).

(4) A method for monitoring an effect of treating pancreatic cancer, the method including: Step (a) of bringing extracellular vesicles, which are in a body fluid sample derived from a subject who has been treated for pancreatic cancer, into contact with one or more kinds of lectins in vitro; Step (b) of measuring an amount of the extracellular vesicles bound to the one or more kinds of lectins after Step (a); and Step (c) of evaluating the presence of pancreatic cancer in the subject based on the amount of the extracellular vesicles measured in Step (b).

(5) A method for collecting data for evaluating an effect of treating pancreatic cancer, the method including: Step (a) of bringing extracellular vesicles, which are in a body fluid sample derived from a subject who has been treated for pancreatic cancer, into contact with one or more kinds of lectins in vitro; Step (b) of measuring an amount of the extracellular vesicles bound to the one or more kinds of lectins after Step (a); and Step (c) of evaluating the presence of pancreatic cancer in the subject based on the amount of the extracellular vesicles measured in Step (b).

(6) Use of lectins and antibodies specifically binding to pan-extracellular vesicle membrane proteins for producing a pancreatic cancer diagnosis kit.

(7) Use of lectins and antibodies specifically binding to pan-extracellular vesicle membrane proteins for diagnosing pancreatic cancer.

(8) Lectins and antibodies specifically binding to pan-extracellular vesicle membrane proteins for use in diagnosis of pancreatic cancer.

In (1) to (8), the lectins preferably include at least one selected from the group consisting of DSA, STL, LEL, ACA, UDA, ABA, MAH, and TJA-1 and more preferably include at least one selected from the group consisting of ABA and ACA. In (1) to (5), Steps (a) to (c) can be performed in the same manner as above. In (7) and (8), examples of pan-extracellular vesicle membrane proteins include CD9, CD63, and CD81.

EXAMPLES

Hereinafter, the present invention will be described using examples, but is not limited to the following examples.

(Selection of Candidate Lectins)

Exosomes were isolated from sera of a pancreatic cancer patient and a healthy subject using Magcapture Exosome Isolation Kit (FUJIFILM Corporation, Tokyo, Japan). The exosomes were redispersed in a buffer and labeled with Cy3-succinimidyl ester (SE; Amersham Biosciences, Tokyo, Japan). This sample was reacted with a lectin array (LecChip (registered trademark), GP Biosciences Ltd., Yokohama, Japan) on which 45 kinds of lectins were immobilized in advance, and exosomes capable of binding to the lectins were immobilized. Such immobilized exosomes were analyzed using an evanescent fluorescence scanner.

As a result, it was found that the amount of exosomes specifically binding to specific lectins increased in the serum of the pancreatic cancer patient. Lectins in which the amount of exosomes binding thereto increased in the serum of the pancreatic cancer patient are shown in Table 1. The p values in Table 1 were calculated using the Mann-Whitney U test. The values in parentheses ( ) indicate 95% confidence intervals (CI).

TABLE 1

| Lectins | Pancreatic cancer patient/healthy subject ratio (95% CI) | p | Preoperative/postoperative ratio |
|---|---|---|---|
| DSA | 1.303 (1.14-1.44) | 0.001 | 0.94 |
| STL | 1.237 (1.09-1.50) | 0.001 | 0.79 |
| LEL | 1.192 (1.05-1.39) | 0.001 | 0.91 |
| ACA | 1.111 (1.02-1.16) | 0.019 | 1.14 |
| UDA | 1.088 (0.99-1.21) | 0.059 | 0.86 |
| ABA | 1.293 (0.88-1.42) | 0.072 | 1.35 |
| MAH | 1.187 (0.81-1.39) | 0.306 | 1.15 |
| TJA-1 | 1.179 (0.96-1.35) | 0.306 | 1.20 |

From the above-described results, it was suggested that it is possible to find or diagnose pancreatic cancer and to monitor the progress degree or the therapeutic effect by detecting exosomes binding to specific lectins.

The results shown in Table 1 were comprehensively evaluated and, and ABA and ACA were selected as candidate lectins and used in the following test.

(Method for Measuring Exosomes Binding to Lectins)

In the subsequent test, measurement of exosomes (hereinafter, also referred to as "ABA/ACA-specific exosomes") having sugar chains binding to ABA or ACA was performed through sandwich immunoassay. The procedure of the sandwich immunoassay performed is shown below.

1) Magnetic beads whose surface is modified with a carboxyl group and to which anti-CD9 antibodies are covalently bound were prepared. Specifically, the following procedure was followed.

PBS (pH 7.4) containing 400 mM 1-ethyl-3-(3-dimethylaminopropyl) carbodiimide hydrochloride (EDC·HCl) and N-hydroxysuccinimide was added to FG beads (COOH beads; Tamagawa Seiki Co., Ltd.) to cause a reaction at room temperature for 4 hours.

The beads were washed with a 50 mM acetate buffer (pH 5.2).

An acetate buffer (pH 5.2) containing 1.0 g/L anti-CD9 antibodies or anti-CD63 antibodies was added to the beads, and a reaction was caused at 4° C. overnight to immobilize the antibodies.

PBS (pH 7.4) containing 0.1 M ethanolamine was added to the beads, and a reaction was caused at 4° C. for 5 hours to mask unreacted carboxyl groups.

The reactant was washed with HEPES buffer (10 mM HEPES, pH 7.9) containing 150 mM KCl, 5 mM EDTA, and 0.1% Tween 20 and preserved at 4° C.

2) ABA or ACA was bound to a disk (extracellular vesicle capture unit) of ExoCounter (registered trademark) (JVC Kenwood, Yokohama, Japan). Specifically, a carbonate buffer (pH 9.6) containing 5 mg/mL lectins was added to the disk and allowed to stand at 37° C. for 30 minutes.

3) The disk was washed with 0.05% PBS-T (pH 7.4).

4) A cancer cell line culture supernatant or subject's serum was appropriately diluted with a buffer solution (PBS or PBS-T) to cause a reaction with ABA or ACA on the disk (shaken at 37° C. for 2 hours at 1,000 to 1,500 rpm).

5) The disk was washed with 0.05% PBS-T (pH 7.4).

6) The magnetic beads to which the anti-CD9 antibodies were bound were suspended in 0.05% PBS-T (pH 7.4) so as to have a concentration of 20 µg/mL and were reacted with exosomes bound to ABA or ACA on the disk (37° C., 1.5 hours). This reaction may be caused through a method for causing a reaction by rapidly collecting magnetism on the surface of the disk using a magnet.

7) The disk was washed with PBS-T. The final washing was performed with pure water.

8) The disk was dried.

9) The disk was set in ExoCounter to measure the exosomes.

In the above-described procedure, the capturing of exosomes on a detection disk was performed with lectins (ABA or ACA) and exosomes were detected with nanobeads on which antibodies against CD9, which is thought to be ubiquitously expressed in exosomes, were immobilized, to detect the ABA/ACA-specific exosomes. In a case where serum was used in 4) described above, the serum was diluted with PBS-T by 4 times.

(Evaluation of Candidate Lectins Using Cancer Cell Lines)

<<Measurement of Number of ABA/ACA-Specific Exosomes>>

It was studied whether there was a difference in the number of ABA/ACA-specific exosomes among cancer types using culture supernatants of various cancer cell lines (pancreatic cancer cell lines: BxPC33 and Capan-1; breast cancer cell line: MCF7; colorectal cancer cell line: HCT116; and lung cancer cell line: A549). The quantitative determination of ABA/ACA-specific exosomes was performed through the method described in (Method for Measuring Exosomes Binding to Lectins) described above.

Figure 4:
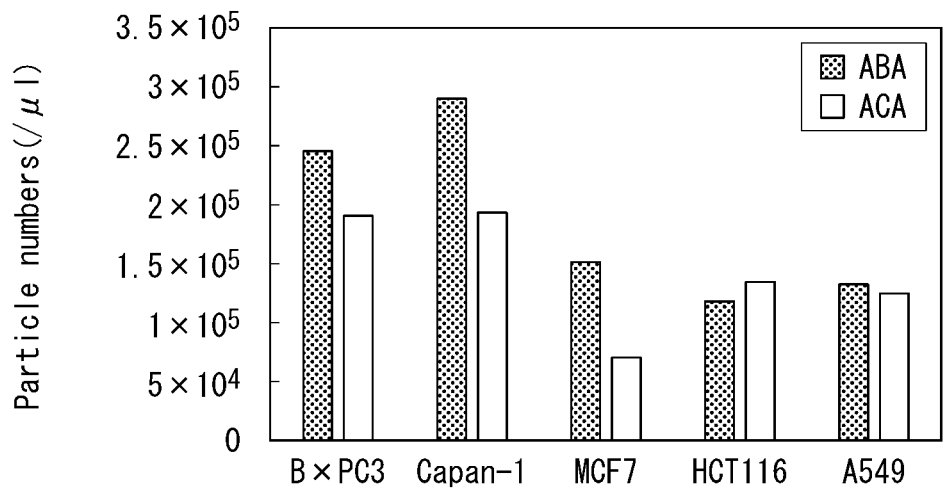
FIG. 4 shows results obtained by measuring the number of exosomes (hereinafter, also referred to as "ABA/ACA-specific exosomes") having a sugar chain binding to ABA or ACA using culture supernatants of various cancer cell lines (pancreatic cancer cell lines: BxPC33 and Capan-1; breast cancer cell line: MCF7; colorectal cancer cell line: HCT116; and lung cancer cell line: A549).

The results are shown in FIG. 4. Exosomes specific to both ABA and ACA lectins could be detected in all the cancer cell lines. Among these, high values of exosomes binding to ABA and ACA were particularly detected using BxPC3 and Capan-1 which were pancreatic cancer cell lines.

<<Ratio of Number of ABA/ACA-Specific Exosomes to Total Number of Exosomes>>

The number of exosomes secreted varies depending on the type of cell line. For this reason, the ratio of ABA/ACA-specific exosomes to the total amount of exosomes secreted is important. Therefore, exosomes were captured on a disk, on which anti-CD63 antibodies were immobilized, using the same sample as described above to detect exosomes using beads on which anti-CD9 antibodies were immobilized. CD63 is, similarly to CD9, a membrane protein which is thought to be ubiquitously expressed in exosomes. For this reason, it can be considered that this measurement result represents the total number of exosomes in the sample. The ratio of ABA- or ACA-specific exosomes to the total exosomes was evaluated by normalizing the measurement values shown in FIG. 4 by the measurement values of CD63 and CD9 using this measurement value.

Figure 5:
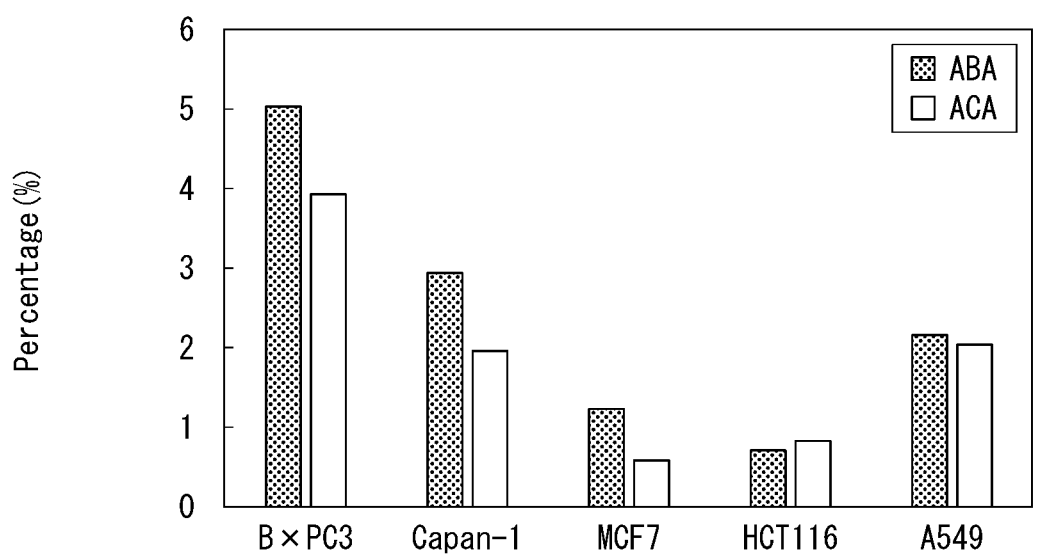
FIG. 5 shows results obtained by calculating rates of the number of ABA/ACA-specific exosomes to the total number of exosomes in the culture supernatants used in FIG. 4.

The results are shown in FIG. 5. It was shown that the proportion of ABA/ACA-specific exosomes in the total exosomes in pancreatic cancer cell lines (BxPC3, Capan-1) was a significantly high value compared to other cancer cell lines.

Example 1

Comparison in Number of ABA/ACA-Specific Exosomes Between Healthy Subject and Pancreatic Cancer Patient It was studied whether there was a difference in the amount of ABA/ACA-specific exosomes between healthy subjects' sera and preoperative and postoperative sera from pancreatic cancer patients. The quantitative determination of ABA/ACA-specific exosomes was performed through the method described in (Method for Measuring Exosomes Binding to Lectins) described above. The sera were diluted 4 times with PBS-T before use.

Figure 6:
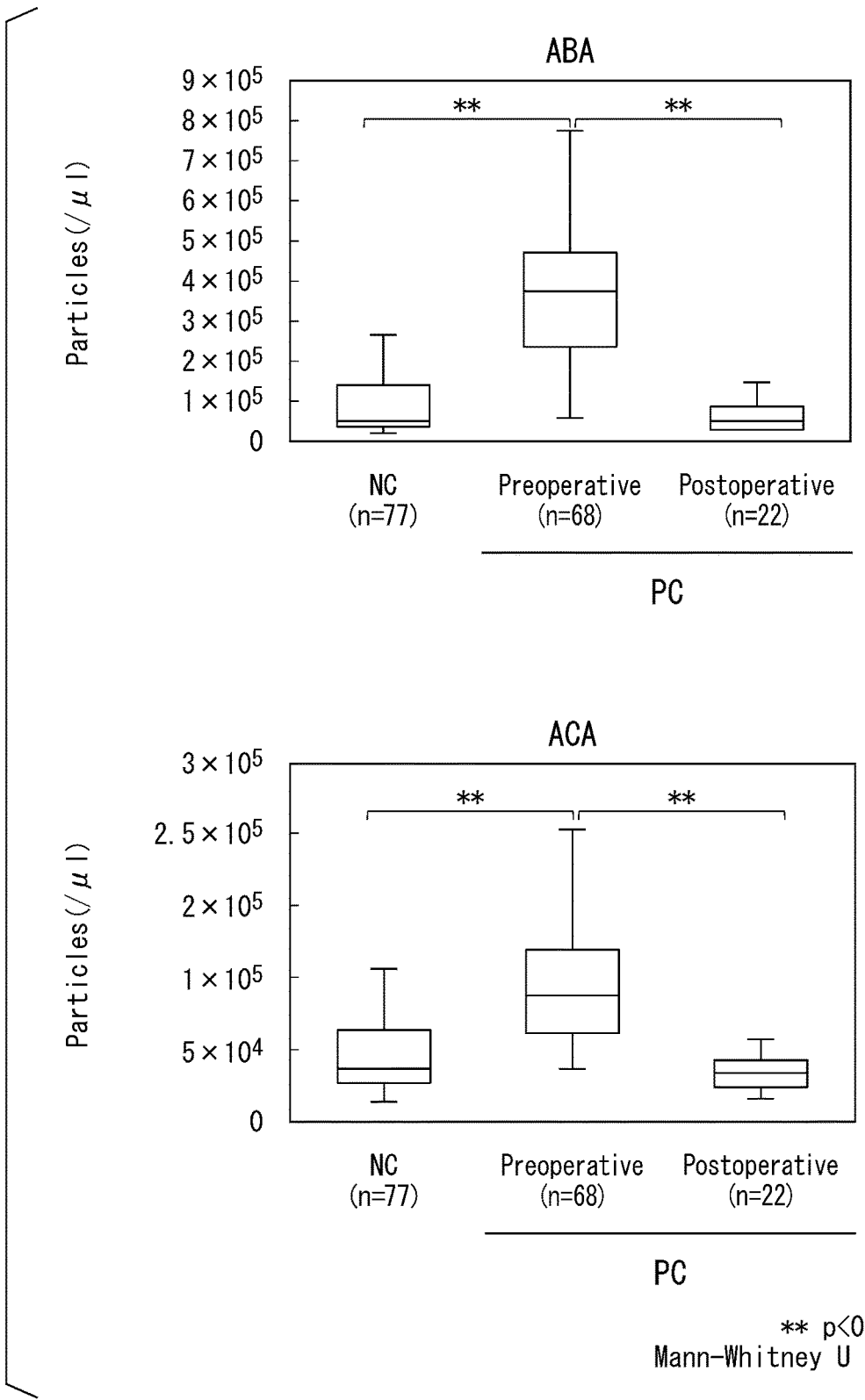
FIG. 6 shows results obtained by measuring the number of ABA/ACA-specific exosomes using healthy subjects' sera (NC) and preoperative (PC/Preoperative) and postoperative (PC/Postoperative) sera of pancreatic cancer patients.

The results are shown in FIG. 6. In the preoperative serum (PC/Preoperative) of the pancreatic cancer patient, both the ABA-specific exosomes and ACA-specific exosomes were statistically significantly higher than those in the healthy subjects' sera (NC). On the other hand, the exosomes in both cases decreased in the postoperative sera (PC/Postoperative) of the pancreatic cancer patients with respect to the preoperative sera, and the difference therebetween was statistically significant. It was shown from the results that the ABA-specific exosomes and the ACA-specific exosomes can be used for detecting pancreatic cancer and monitoring recurrence of pancreatic cancer after surgery.

Example 2

Comparison in Number of ABA/ACA-Specific Exosomes Between Pancreatic Cancer and Other Cancer Types It was studied whether there was a difference in the amount of ABA/ACA-specific exosomes between cancer types from healthy subjects' sera and sera from each of pancreatic cancer patients, esophageal cancer patients, and colorectal cancer patients. The quantitative determination of ABA/ACA-specific exosomes was performed through the method described in (Method for Measuring Exosomes Binding to Lectins) described above.

Figure 7:
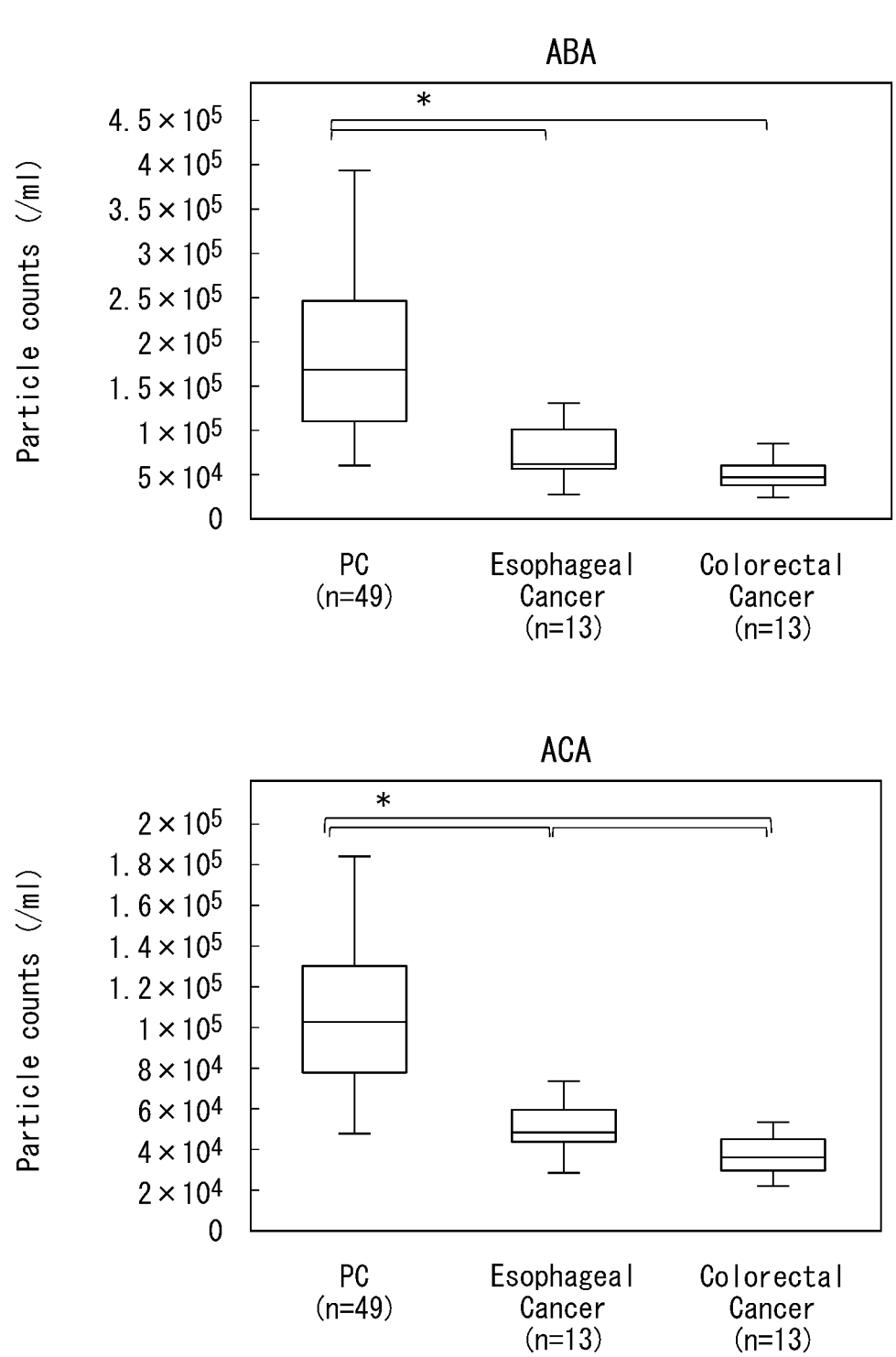
FIG. 7 shows results obtained by measuring the number of ABA/ACA-specific exosomes using s pancreatic cancer patients' sera (PC), esophageal cancer patients' sera (Esophageal Cancer), and colorectal cancer patients' sera (Colorectal Cancer).

The results are shown in FIG. 7. In the pancreatic cancer patients' sera (PC), both ABA-specific exosomes and ACA-specific exosomes were higher than those in the esophageal cancer patients' sera (Esophageal Cancer) and the colorectal cancer patients' sera (Colorectal Cancer). It was shown from the results that the ABA-specific exosomes and the ACA-specific exosomes are effective for specifically detecting pancreatic cancer.

Example 3

Comparison in Number of ABA/ACA-Specific Exosomes Between Pancreatic Cancer Patients at Different Stages It was studied whether there was a difference in the amount of ABA/ACA-specific exosomes between sera from a healthy subjects' sera and pancreatic cancer patients' sera at Stages I, II, and III. The quantitative determination of ABA/ACA-specific exosomes was performed through the method described in (Method for Measuring Exosomes Binding to Lectins) described above.

Figure 8:
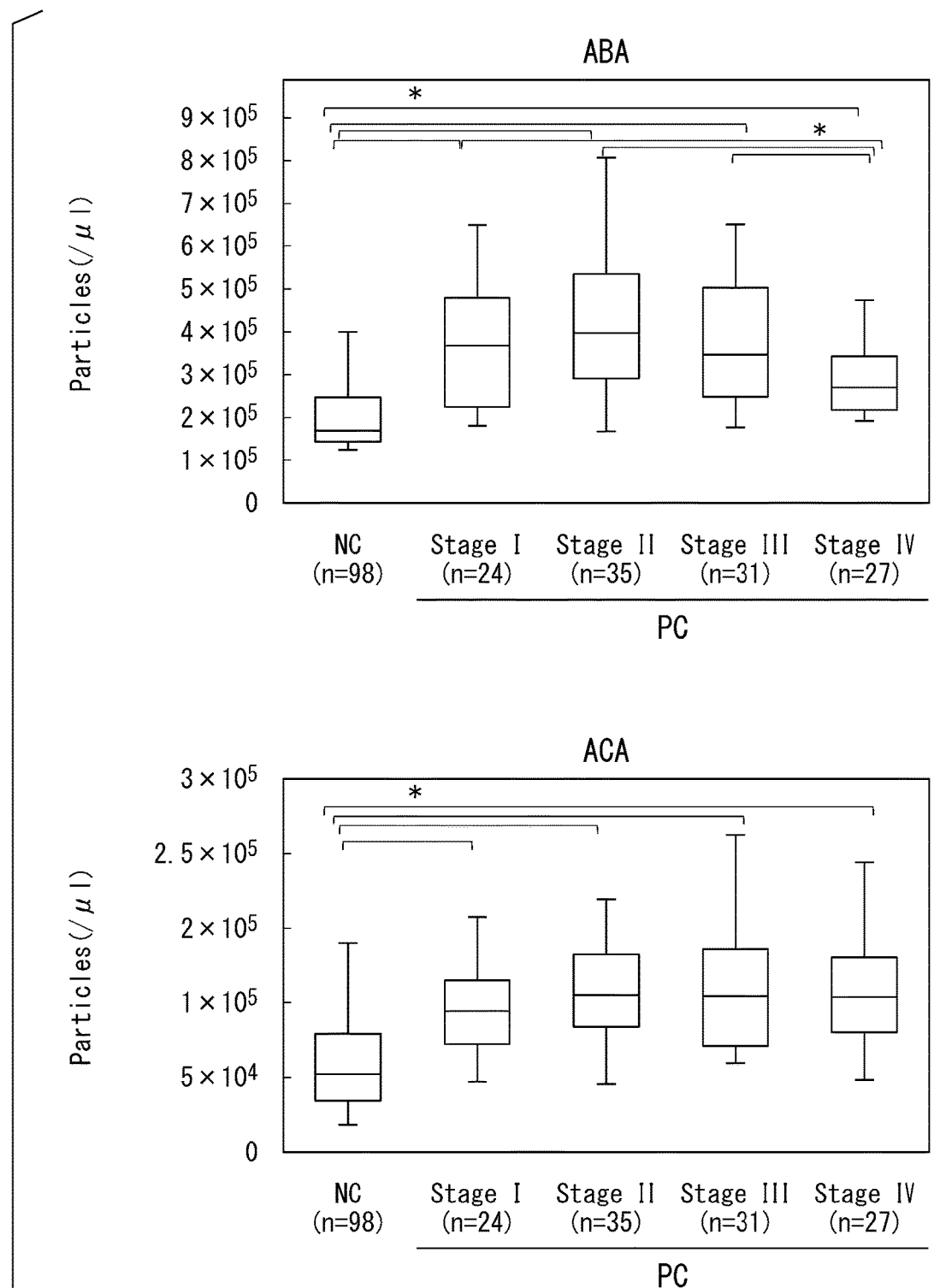
FIG. 8 shows results obtained by measuring the number of ABA/ACA-specific exosomes using healthy subjects' sera (NC) and each pancreatic cancer patients' sera of Stage I to III.

The results are shown in FIG. 8. In the pancreatic cancer patients' sera at Stage I, both the ABA-specific exosomes and ACA-specific exosomes were also statistically significantly higher than those in the healthy subjects' sera (NC). It was shown from the results that the ABA/ACA-specific exosomes are effective for early detection of pancreatic cancer.

According to the present invention, a pancreatic cancer detection method and a pancreatic cancer detection kit are provided which enable early detection of pancreatic cancer and monitoring of a therapeutic effect through a liquid biopsy.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

EXPLANATION OF REFERENCES

1 Solid-phase carrier
2 Concave portion
3 Convex portion
10 Lectin
21, 22, 23 Sugar chain
31 Pan-extracellular vesicle membrane protein
40 Solid-phase carrier particle
41 Antibody specifically binding to pan-extracellular vesicle membrane protein
50 Extracellular vesicle capture unit
51 Substrate
52 Cartridge
55 Track region
56 Through-hole
57 Well

What is claimed is:

1. A pancreatic cancer detection method comprising:
   (a) bringing extracellular vesicles, which are in a body fluid sample derived from a subject, into contact with one or more kinds of lectins;
   (b) measuring an amount of the extracellular vesicles bound to the one or more kinds of lectins after (a); and
   (c) evaluating presence of pancreatic cancer in the subject based on the amount of the extracellular vesicles measured in (b),
   wherein the evaluation of the presence of the pancreatic cancer is applied in treating the pancreatic cancer in the subject having pancreatic cancer who is identified in (c).

2. The pancreatic cancer detection method according to claim 1, wherein (c) comprises
   evaluating that pancreatic cancer is present in the subject in a case where the amount of the extracellular vesicles measured in (b) is larger than that of extracellular vesicles binding to the one or more kinds of lectins measured using a body fluid sample from a subject known to not have pancreatic cancer.

3. The pancreatic cancer detection method according to claim 1, wherein the one or more kinds of lectins include at least one selected from the group consisting of DSA (*Datura stramonium* agglutinin), STL (*Solanum tuberosum* lectin), LEL (*Lycopersicon esculentum* lectin), ACA (*Amaranthus caudatus* agglutinin), UDA (*Urtica dioica* agglutinin), ABA (*Agaricus bisporus* agglutinin), MAH (*Maackia amurensis* hemagglutinin), and TJA-1 (*Trichosanthes japonica* agglutinin I).

4. The pancreatic cancer detection method according to claim 1, wherein (b) is performed using an antibody specifically binding to a pan-extracellular vesicle membrane protein or an antigen-binding fragment thereof.

5. The pancreatic cancer detection method according to claim 4, wherein the pan-extracellular vesicle membrane protein is selected from the group consisting of CD9, CD63, and CD81.

6. A method for treating pancreatic cancer:
   (a) bringing extracellular vesicles, which are in a body fluid sample derived from a subject, into contact with one or more kinds of lectins;
   (b) measuring an amount of the extracellular vesicles bound to the one or more kinds of lectins after (a);
   (c) identifying the subject having pancreatic cancer based on the amount of the extracellular vesicles measured in (b); and
   (d) treating the pancreatic cancer in the subject having pancreatic cancer who is identified in (c).

7. The method according to claim 6,
   wherein (c) comprises
   identifying the subject in which the amount of the extracellular vesicles measured in (b) is larger than that of extracellular vesicles binding to the one or more kinds of lectins measured using a body fluid sample from a subject known to not have pancreatic cancer, as the subject having pancreatic cancer.

8. The method according to claim 6, wherein the one or more kinds of lectins include at least one selected from the group consisting of DSA (*Datura stramonium* agglutinin), STL (*Solanum tuberosum* lectin), LEL (*Lycopersicon esculentum* lectin), ACA (*Amaranthus caudatus* agglutinin), UDA (*Urtica dioica* agglutinin), ABA (*Agaricus bisporus* agglutinin), MAH (*Maackia amurensis* hemagglutinin), and TJA-1 (*Trichosanthes japonica* agglutinin I).

9. The method according to claim 6, wherein (b) is performed using an antibody specifically binding to a pan-extracellular vesicle membrane protein or an antigen-binding fragment thereof.

10. The method according to claim 9, wherein the pan-extracellular vesicle membrane protein is selected from the group consisting of CD9, CD63, and CD81.

* * * * *